United States Patent
Xu et al.

(10) Patent No.: US 11,162,959 B2
(45) Date of Patent: Nov. 2, 2021

(54) TIME-RESOLVED FLUORESCENT IMMUNOCHROMATOGRAPHIC TEST STRIP FOR DETECTING VANCOMYCIN AS WELL AS PREPARATION METHOD AND APPLICATION THEREOF

(71) Applicant: BEIJING DIAGREAT BIOTECHNOLOGIES CO., LTD., Beijing (CN)

(72) Inventors: Xiuli Xu, Beijing (CN); Yanxin Wang, Beijing (CN); Yuanrong Chang, Beijing (CN); Jianping Zhou, Beijing (CN)

(73) Assignee: Beijing Diagreat Biotechnologies Co., LTD., Beijing (CN)

( * ) Notice: Subject to any disclaimer, the term of this patent is extended or adjusted under 35 U.S.C. 154(b) by 36 days.

(21) Appl. No.: 16/459,813

(22) Filed: Jul. 2, 2019

(65) Prior Publication Data

US 2020/0217860 A1    Jul. 9, 2020

(30) Foreign Application Priority Data

Jan. 9, 2019    (CN) .................. 201910020000.0

(51) Int. Cl.
| | | |
|---|---|---|
| *G01N 33/558* | (2006.01) | |
| *G01N 33/543* | (2006.01) | |
| *C07K 14/765* | (2006.01) | |
| *G01N 33/533* | (2006.01) | |
| *G01N 33/94* | (2006.01) | |
| *G01N 33/53* | (2006.01) | |

(52) U.S. Cl.
CPC ....... *G01N 33/9446* (2013.01); *G01N 33/533* (2013.01); *G01N 33/5306* (2013.01); *G01N 33/5432* (2013.01); *G01N 33/54366* (2013.01)

(58) Field of Classification Search
CPC .......... G01N 33/9446; G01N 33/5306; G01N 33/533; G01N 33/5432; G01N 33/54366; G01N 33/558; G01N 33/54313; C07K 9/008; C07K 14/765
See application file for complete search history.

(56) References Cited

FOREIGN PATENT DOCUMENTS

| CN | 103575889 A | * | 2/2014 |
| CN | 103575899 A | * | 2/2014 |
| CN | 106872420 A | * | 6/2017 |

* cited by examiner

*Primary Examiner* — Tracy Vivlemore
*Assistant Examiner* — Nam P Nguyen
(74) *Attorney, Agent, or Firm* — Avant Law Group, LLC

(57) ABSTRACT

Some embodiments of the disclosure provide a time-resolved fluorescent immunochromato-graphic test strip for detecting vancomycin as well as a preparation method and application thereof. In some embodiments, the test strip includes a bottom plate and a sample absorption pad. A fluorescent microsphere pad, a nitrocellulose membrane coated with a vancomycin-carrier protein conjugate, and an absorbent pad are sequentially overlapped and pasted on the bottom plate. The fluorescent microsphere pad is sprayed with a fluorescent microsphere-labeled vancomycin monoclonal antibody, and the vancomycin monoclonal antibody is prepared by using a vancomycin-bovine serum albumin conjugate as an immunogen.

2 Claims, 1 Drawing Sheet

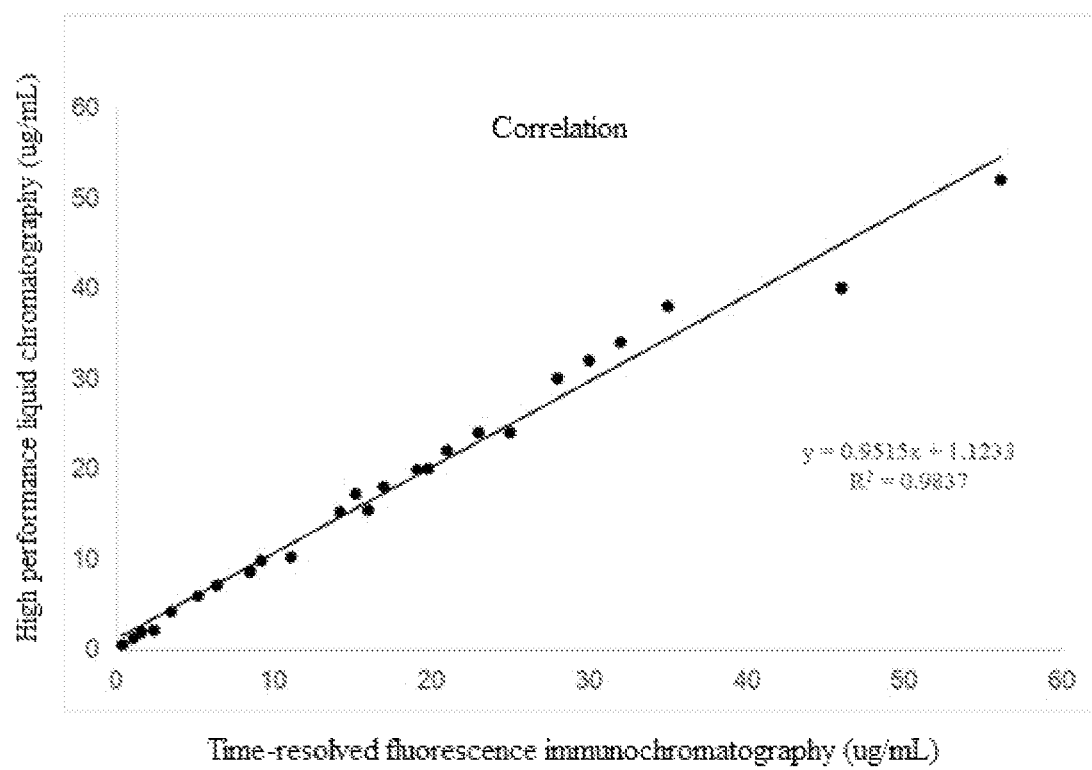

TIME-RESOLVED FLUORESCENT IMMUNOCHROMATOGRAPHIC TEST STRIP FOR DETECTING VANCOMYCIN AS WELL AS PREPARATION METHOD AND APPLICATION THEREOF

CROSS REFERENCE TO RELATED APPLICATIONS

This application claims priority to Chinese application number 20191002000-0.0 filed on Jan. 9, 2019, the disclosure of which is incorporated by reference herein in its entirety.

FIELD OF THE DISCLOSURE

The disclosure relates generally to the field of drug concentration detection of in vitro diagnostic reagents. More specifically, the disclosure relates to the field of a time-resolved fluorescent immunochromatographic test strip for detecting vancomycin as well as a preparation method and application thereof.

BACKGROUND

Vancomycin is a tricyclic glycopeptide antibiotic that is a preferred antibiotic for clinically treating serious infections caused by Methicillin-Resistant *Staphylococcus Aureus* (MRS1), Methicillin-Resistant *Staphylococcus Epidermidis* (MRSE), and Penicillin-Resistant *Streptococcus Pneumoniae* (PRSP). Vancomycin has a strong bactericidal effect on gram-positive bacteria, but is narrow in therapeutic index and significant in individual metabolic difference, and has significant ototoxicity and nephrotoxicity. Therefore, it is necessary to monitor the blood concentration to adjust the medication.

At present, methods for monitoring the concentrations of vancomycin drugs at home and abroad include Thin Layer Chromatography (TL3), Capillary Electrophoresis (CE), High Performance Liquid Chromatography (HPL3), and biochemical methods. However, the methods are not suitable for large-scale clinical promotion. Although Turbidimetric inhibition immuno assay (TI1), homogeneous enzyme immunoassay, chemiluminescence, and fluorescence polarization are currently available on the market for assay of vancomycin, the cost is high, and the methods are monopolized by foreign importers, and cannot meet the ever-increasing demand for clinical monitoring.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

Some embodiments of the disclosure provide a time-resolved fluorescent immunochromatographic test strip for detecting vancomycin as well as a preparation method and an application thereof.

In some embodiments, a preparation method of a vancomycin-bovine serum albumin conjugate includes the following steps: (1) mixing a sodium periodate aqueous solution with a vancomycin aqueous solution to obtain a vancomycin pre-conjugate by a redox reaction; (2) mixing bovine serum albumin with a carbonate buffer to obtain a bovine serum albumin solution; and (3) mixing the vancomycin pre-conjugate in step (1) with the bovine serum albumin solution in step (2) to obtain a vancomycin-bovine serum albumin conjugate by a coupling reaction.

Optionally, Steps (1) and (2) are not chronologically limited.

Optionally, the time of the coupling reaction in step (3) is 10-15 h, and the temperature of the coupling reaction is 15-37° C.

Optionally, the time of the redox reaction in step (1) is 0.8-1.5 h, and the temperature of the redox reaction is 18-26° C.

In other embodiments, the disclosure provides a vancomycin-bovine serum albumin conjugate prepared by the above preparation method.

In further embodiments, the disclosure provides a time-resolved fluorescent immunochromatographic test strip for detecting vancomycin including a bottom plate and a sample absorption pad. A fluorescent microsphere pad, a nitrocellulose membrane coated with a vancomycin-carrier protein conjugate, and an absorbent pad are sequentially overlapped and pasted on the bottom plate. The fluorescent microsphere pad is sprayed with a fluorescent microsphere-labeled vancomycin monoclonal antibody. The vancomycin monoclonal antibody is prepared by using the above vancomycin-bovine serum albumin conjugate as an immunogen.

Optionally, the diameter of the fluorescent microsphere is 100-300 nm, and the fluorescent microsphere has a carboxyl group on the surface.

Optionally, the fluorescent microsphere includes rare earth ions Eu+ coated with polystyrene.

Optionally, a preparation method of a fluorescent microsphere-labeled vancomycin monoclonal antibody includes the steps of: (1) mixing a fluorescent microsphere suspension, an MES buffer, 1-(3-dimethylaminopropyl)-3-ethylcarbodiimide, and N-hydroxysuccinimide for activation treatment to obtain an activated fluorescent microsphere; and (2) mixing the activated fluorescent microsphere in step (1) with the vancomycin monoclonal antibody for coupling to obtain a fluorescent microsphere-labeled vancomycin monoclonal antibody.

Some embodiments of the disclosure provide an application of a test strip in detection of vancomycin including the following steps. (1) Adding pure vancomycin of different concentrations to a human serum matrix excluding vancomycin to prepare a calibrator. The concentrations of vancomycin in the calibrator are 40 µg/mL, 20 µg/mL, 10 µg/mL, 5 µg/mL, and 0 µg/mL, sequentially. (2) Diluting the calibrator 100-1,000 times and loading to a sample absorption pad of the test strip for immunochromatography. (3) Determining a ratio (a T/C ratio) of the time-resolved fluorescent intensity of a detection area to the time-resolved fluorescent intensity of a quality control area to obtain a function relation of the concentration of the calibrator and the T/C ratio. (4) Taking a sample to be tested and loading it to the sample absorption pad of the test strip for immunochromatography. (5) Determining a ratio of the time-resolved fluorescent intensity of the detection area to the time-resolved fluorescent intensity of the quality control area. (6) Calculating the content of vancomycin in the sample to be tested according to the obtained function formula.

Optionally, the sample to be tested is loaded in an amount of 1-100 µL.

BRIEF DESCRIPTION OF THE DRAWINGS

The FIGURE is a graph showing the correlation analysis of the measurement results of the test strips of Embodiment 1 of the disclosure in Embodiment 4.

DETAILED DESCRIPTION

Some embodiments of the disclosure provide a preparation method of a vancomycin-bovine serum albumin conjugate including the steps of: (1) a sodium periodate aqueous solution is mixed with a vancomycin aqueous solution to obtain a vancomycin pre-conjugate by a redox reaction; (2) bovine serum albumin is mixed with a carbonate buffer to obtain a bovine serum albumin solution; and (3) the vancomycin pre-conjugate in step (1) is mixed with the bovine serum albumin solution in step (2), and a coupling reaction is carried out to obtain a vancomycin-bovine serum albumin conjugate. Optionally, steps (1) and (2) may or may not be chronologically limited.

In the disclosure, one of the reasons for preparing the vancomycin-bovine serum albumin conjugate may be that vancomycin is a small molecule substance, which may be immunoreactive, have no immunogenicity, and/or cannot induce an immune response in the body. Therefore, coupling vancomycin with a carrier protein may make vancomycin immunogenic. The structural formula of vancomycin (Vm) hydrochloride is as follows:

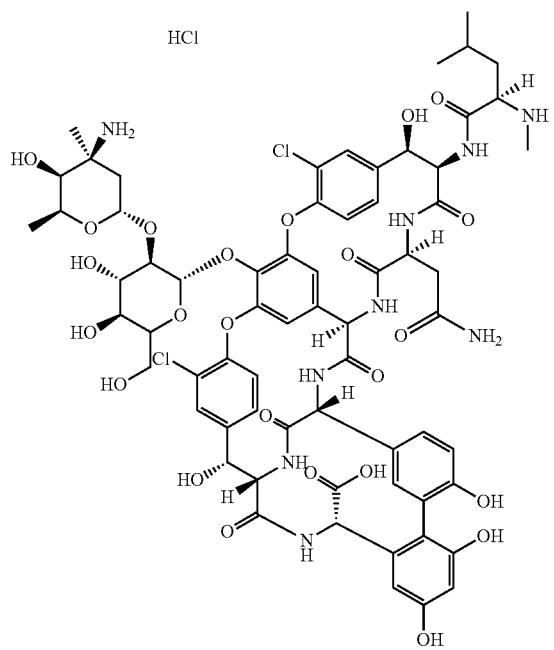 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O)c3ccc(c(Cl)c3)Oc3cc2cc(c3O[C@@H]2OC(CO)[C@@H](O)[C@H](O)[C@H]2O[C@H]2C[C@](C)(N)[C@H](O)[C@H](C)O2)Oc2ccc(cc2Cl)[C@H]1O ; Cl]

In the disclosure, the sodium periodate aqueous solution is mixed with the vancomycin aqueous solution to obtain a vancomycin pre-conjugate by a redox reaction.

In the disclosure, the concentration of the sodium periodate aqueous solution may be 8-12 mg/mL and preferably 10 mg/mL, and the concentration of the vancomycin aqueous solution may be 8-12 mg/mL and preferably 10 mg/mL. The solvent of the vancomycin aqueous solution may be ultra-pure water. The volume ratio of the sodium periodate aqueous solution to the vancomycin aqueous solution may be 1-3:0.5-1.5 and preferably 2:1.

In the disclosure, the time of the redox reaction may be 0.8-1.5 h and preferably 1-1.2 h. the temperature of the redox reaction may be 18-26° C. and preferably 20° C. The redox reaction may be carried out in the dark. The redox reaction may be carried out under stirring. The stirring speed may be 500-3,000 rpm, preferably 800-2,000 rpm, and more preferably 1,500 rpm.

In the disclosure, the bovine serum albumin is mixed with the carbonate buffer to obtain a bovine serum albumin solution.

In the disclosure, the mass/volume ratio of the bovine serum albumin to the carbonate buffer is 4-6 mg:0.5-1.5 mL and preferably 5 mg:1 mL. The concentration of the carbonate buffer may be 40-60 mmol/L and preferably 50 mmol/L. The pH of the carbonate buffer may be 9.4-9.8 and preferably 9.6. The mixing temperature may be 15-37° C., preferably 20-30° C., and more preferably 25° C. The mixing time may be 0.5-3 h, preferably 1-2 h, and more preferably 1.5 h.

In the disclosure, after the vancomycin pre-conjugate and the bovine serum albumin solution are obtained, the vancomycin pre-conjugate is mixed with the bovine serum albumin solution to obtain a vancomycin-bovine serum albumin conjugate by a coupling reaction.

In the disclosure, the volume ratio of the vancomycin pre-conjugate to the bovine serum albumin solution may be 1-2:0.5-1.5 and preferably 1.5:1. The time of the coupling reaction may be 10-15 h and preferably 12 h. The temperature of the coupling reaction may be 15-37° C. and preferably 25° C. The coupling reaction may be carried out under stirring. The stirring speed may be 500-3,000 rpm, preferably 800-2,000 rpm, and more preferably 1,500 rpm.

After the vancomycin pre-conjugate is mixed with the bovine serum albumin solution, the disclosure optionally further includes adjusting the pH. The adjusted pH may be 8.5-9.5 and preferably 9. The reagent for adjusting the pH may be a sodium carbonate solution. The concentration of the sodium carbonate solution may be 0.5-1.5 mol/L and preferably 1 mol/L.

After the coupling reaction, the disclosure optionally further includes dialyzing the coupling reactant against water, using an 8K interception dialysis bag for more than 12 h per dialysis to remove unreacted vancomycin molecules and a coupling agent. The number of times of dialysis against water may be 3-7, and preferably 5.

After the vancomycin-bovine serum albumin conjugate is obtained by the disclosure, the vancomycin-bovine serum albumin conjugate may be stored at −40° C. to −80° C. and preferably −70° C.

After the vancomycin-bovine serum albumin conjugate is obtained, the disclosure optionally further includes: identifying the vancomycin-bovine serum albumin conjugate. The method for identifying includes the following step. The molecular weight of the vancomycin-bovine serum albumin conjugate is compared with that of bovine serum albumin. It is indicated that vancomycin has been successfully coupled to bovine serum albumin when the molecular weight of the vancomycin-bovine serum albumin conjugate is significantly greater than that of bovine serum albumin. The manner of molecular weight determination may be Native SDS-PAGE electrophoresis.

The disclosure provides a vancomycin-bovine serum albumin conjugate prepared by the preparation method according to the foregoing solution. The vancomycin conjugate is immunogenic and can be used as an immunogen for preparing a vancomycin monoclonal antibody.

The disclosure provides a time-resolved fluorescent immunochromatographic test strip for detecting vancomycin, including a bottom plate and a sample absorption pad, a fluorescent microsphere pad, a nitrocellulose membrane coated with an antibody, and an absorbent pad which are sequentially overlapped and pasted on the bottom plate.

In the disclosure, the test strip may be assembled by the following method: the sample absorption pad, the fluorescent microsphere pad, the nitrocellulose membrane coated with the vancomycin-carrier protein conjugate, and the absorbent pad are overlapped and pasted onto the bottom plate sequentially from left to right. The end of the sample absorption pad is connected to the beginning of the fluorescent microsphere pad, the end of the fluorescent microsphere pad is connected to the beginning of the nitrocellulose membrane coated with the vancomycin-carrier protein conjugate, the end of the nitrocellulose membrane coated with the vancomycin-carrier protein conjugate is connected to the beginning of the absorbent pad, the beginning of the sample absorption pad is aligned with the beginning of the bottom plate, and the end of the absorbent pad is aligned with the end of the bottom plate, and then cut into small strips by a machine to be packed in a special plastic card to form a test strip, the width of the small strip may be 3.8-4 mm and preferably 3.96 mm.

In the disclosure, the sample absorption pad may be prepared a method including the following step: the absorbent pad is placed in the bovine serum albumin solution, soaked, and dried to obtain the sample absorption pad In the disclosure, the volume percentage of bovine serum albumin in the bovine serum albumin solution may be 0.3-0.8% and preferably 0.5%. The solvent of the bovine serum albumin solution may be a phosphate buffer. The concentration of the phosphate buffer may be 0.05-0.15 mol/L and preferably 0.1 mol/L. The pH of the phosphate buffer may be 7.1-7.5 and preferably 7.2. The soaking time may be 1.5-2.5 h and preferably 2 h. The soaking temperature may be 15-37° C. and preferably 25° C. The drying temperature may be 35-40° C. and preferably 37° C. The drying time may be 1-3 h and preferably 2 h. The drying mode may be oven-drying.

In the disclosure, the fluorescent microsphere pad is sprayed with the fluorescent microsphere-labeled vancomycin monoclonal antibody. The fluorescent microsphere pad may be prepared by the following method: the fluorescent microsphere-labeled vancomycin monoclonal antibody is loaded to a glass cellulose membrane and dried to obtain a fluorescent microsphere pad. The fluorescent microsphere-labeled vancomycin monoclonal antibody may be added in an amount of 10-100 preferably 20-50 and more preferably 30 μg. A loading device of the fluorescent microsphere-labeled vancomycin monoclonal antibody may be a gold-standard film sprayer. The drying time may be 12-18 h and preferably 15 h. The drying temperature may be 35-40° C. and preferably 37° C.

In the disclosure, the fluorescent microsphere-labeled vancomycin monoclonal antibody may be prepared by the following method. (1) A fluorescent microsphere suspension, an MES buffer, 1-(3-dimethylaminopropyl)-3-ethylcarbodiimide, and N-hydroxysuccinimide are mixed for activation treatment to obtain an activated fluorescent microsphere. (2) The activated fluorescent microsphere in step (1) is mixed with the vancomycin monoclonal antibody for coupling to obtain a fluorescent microsphere-labeled vancomycin monoclonal antibody.

In the disclosure, the fluorescent microsphere suspension, the MES buffer, 1-(3-dimethylaminopropyl)-3-ethylcarbodiimide, and N-hydroxysuccinimide are mixed for activation treatment to obtain an activated fluorescent microsphere.

In the disclosure, the diameter of the fluorescent microsphere is 100-300 nm, preferably 150-280 nm, and more preferably 200 nm. Optionally, the fluorescent microsphere has a carboxyl group on the surface. The fluorescent microsphere optionally includes rare earth ions Eu+ coated with polystyrene. The content of the fluorescent microsphere in the fluorescent microsphere suspension may be 1% (W/V). The concentration of the MES may be 40-60 mM and preferably 50 mM. The pH of the MES buffer may be 5.5-6.5 and preferably 6. The ratio of the fluorescent microsphere suspension, the MES buffer, 1-(3-dimethylaminopropyl)-3-ethylcarbodiimide, and N-hydroxysuccinimide is 80-120 μL:300-500 μL:0.3-1 mg:0.3-1 mg and preferably 100 μL:400 μL:0.5 mg:0.5 mg. In the disclosure, the time for activation treatment may be 10-20 min and preferably 15 min. The temperature for activation treatment may be 18-26° C. and preferably 20° C. The activation treatment may be carried out in an oscillating condition.

After the activated fluorescent microsphere is obtained, the disclosure optionally further includes centrifuging the activated fluorescent microsphere, and re-suspending precipitates. The centrifugal rotation speed may be 8,000-12,000 rpm and preferably 10,000 rpm. The centrifuging temperature may be 0-5° C. and preferably 4° C. The centrifuging time may be 8-12 min and preferably 10 min. The solvent for re-suspending precipitates may be the MES buffer.

In the disclosure, the activated fluorescent microsphere is mixed with the vancomycin monoclonal antibody for coupling to obtain a fluorescent microsphere-labeled vancomycin monoclonal antibody.

In the disclosure, the volume mass ratio of the activated fluorescent microsphere to the vancomycin monoclonal antibody may be 400-600 μL:1-3 μg and preferably 500 μL:2 μg. The time for coupling may be 100-150 min and preferably 120 min. The temperature for coupling may be 18-26° C. and preferably 20° C. The coupling may be carried out in an oscillating condition.

After the fluorescent microsphere-labeled vancomycin monoclonal antibody is obtained, the disclosure optionally further includes: the fluorescent microsphere-labeled vancomycin monoclonal antibody is mixed with the bovine serum albumin aqueous solution for a blocking treatment to obtain a blocked fluorescent microsphere-labeled vancomycin monoclonal antibody. The volume ratio of the fluorescent microsphere-labeled vancomycin monoclonal antibody to the bovine serum albumin aqueous solution may be 4-6:0.5-1.5 and preferably 5:1 The mass percentage of bovine serum albumin in the bovine serum albumin aqueous solution may be 8-12% and preferably 10%. The blocking temperature may be 18-26° C. and preferably 20° C. The blocking time may be 10-15 h and preferably 12 h.

In the disclosure, the method for storing the blocked fluorescent microsphere-labeled vancomycin monoclonal antibody includes the following steps. The blocked fluorescent microsphere-labeled vancomycin monoclonal antibody is centrifuged. Precipitates are re-suspended and washed, and then saved. In the disclosure, the centrifugal rotation speed may be 8,000-12,000 rpm and preferably 10,000 rpm. The centrifuging temperature may be 0-5° C. and preferably 4° C. The centrifuging time may be 8-12 min and preferably 10 min. The solvent for re-suspending the precipitates may be a storage buffer. The storage buffer may be a phosphate buffer containing NaN3 and bovine serum albumin. The mass percentage of NaN3 in the phosphate buffer may be 0.01-0.02%. The mass percentage of bovine serum albumin in the phosphate buffer may be 0.1-0.2%. The pH of the phosphate buffer may be 7.2-7.5 and preferably 7.4. The number of times of washing precipitates may be 1-2. The method for washing precipitates includes centrifuging again, and re-suspending the precipitates. The temperature of storage may be 0-5° C. and preferably 4° C. The storage may be carried out in the dark.

Optionally, the vancomycin monoclonal antibody is prepared by using the vancomycin-bovine serum albumin conjugate as described in the scheme as an immunogen and more Optionally, the vancomycin monoclonal antibody is prepared by the following steps.

(1) The vancomycin-bovine serum albumin conjugate as described in the scheme is used as an immunogen to immunize a first Balb/c mouse, and immunization is boosted to obtain Balb/c mouse spleen cells capable of producing specific antibodies.

(2) The Balb/c mouse spleen cells capable of producing specific antibodies in step (1) are fused with myeloma cells SP20, a cell supernatant is determined, and positive wells are screened.

(3) Cloning the fused cells in the positive wells in step (2) to obtain monoclonal antibody-producing hybridoma cells.

(4) The hybridoma cells in step (3) are intraperitoneally injected after the sterilized paraffin oil is injected into the abdominal cavity of a second Balb/c mouse, and ascites is collected and purified to obtain a vancomycin monoclonal antibody.

In the disclosure, the first Balb/c mouse is immunized by using the vancomycin-bovine serum albumin conjugate as the immunogen as described in the scheme, to obtain Balb/c mouse spleen cells capable of producing specific antibodies.

The disclosure has no special limitation to the immunization method, and the conventional immunization methods in the art can be used. The disclosure has no special requirement for the number of booster immunizations and the dosage of vancomycin-bovine serum albumin conjugate for each booster immunization on the basis that the first Balb/c mouse can produce specific antibodies. The disclosure has no special limitation to the method for obtaining Balb/c mouse spleen cells capable of producing specific antibodies, and the conventional immunization methods in the art can be used.

In the disclosure, after Balb/c mouse spleen cells capable of producing specific antibodies are obtained, the Balb/c mouse spleen cells capable of producing specific antibodies are fused with myeloma cells SP20, the cell supernatant is determined, and positive wells are screened.

In the disclosure, the method for determining the cell supernatant may be an indirect competitive enzyme-linked immunoassay. The disclosure has no special limitation to the method for screening the positive wells, and the conventional screening methods in the art can be used.

In the disclosure, after the positive wells are obtained, the fused cells in the positive wells are cloned to obtain monoclonal antibody-producing hybridoma cells. The disclosure has no special limitation to the method for cloning, and the conventional methods in the art can be used.

In the disclosure, after the hybridoma cells are obtained, the hybridoma cells are intraperitoneally injected after the sterilized paraffin oil is injected into the abdominal cavity of the second Balb/c mouse, and ascites is collected and purified to obtain the vancomycin monoclonal antibody.

In the disclosure, the age of the second Balb/c mouse may be 7-9 weeks old and preferably 8 weeks old. The disclosure has no special limitation to the injection amount of the sterilized paraffin oil, and the conventional dosages in the art can be used. The time interval between the intraperitoneal injection of the sterile paraffin oil in the second Balb/c mouse and the intraperitoneal injection of the hybridoma cells may be 7-14 d and preferably 10-12 d. The time interval between the intraperitoneal injection of the hybridoma cells and the ascites collection may be 7-10 d and preferably 8-9 d. The method for purifying ascites may be an octanoic acid-saturated ammonium sulfate method.

After the ascites is purified, the disclosure optionally further includes the purity identification of the vancomycin monoclonal antibody. The method for identification may be SDS-PAGE electrophoresis.

In the specific implementation process of the disclosure, the storage temperature of the vancomycin monoclonal antibody may be from −15° C. to −30° C. and preferably −20° C.

In the disclosure, the nitrocellulose membrane coated with the vancomycin-carrier protein conjugate optionally includes a detection area (T) and a quality control area (C). The detection area may be coated with a vancomycin-chicken egg albumin conjugate, and the quality control area may be coated with a goat anti mouse antibody. In the disclosure, the nitrocellulose membrane coated with the vancomycin-carrier protein conjugate may be prepared by the following method: the detection area is coated with the vancomycin-chicken egg albumin conjugate, the quality control area is coated with the goat anti mouse antibody, and dried to obtain a nitrocellulose membrane coated with the vancomycin-carrier protein conjugate. The drying temperature may be 35-40° C. and preferably 37° C. The drying time may be 4-6 h and preferably 5 h.

In the disclosure, coating the detection area with the vancomycin-chicken egg albumin conjugate may be carried out by the following method: the vancomycin-chicken egg albumin conjugate is sprayed onto a detection region on the nitrocellulose membrane to form the detection area. In the disclosure, the concentration of the vancomycin-chicken egg albumin conjugate may be 150-280 μg/mL and preferably 200 μg/mL. The spraying amount of the vancomycin-chicken egg albumin conjugate may be 1-1.5 μL/cm and preferably 1.2 μL/cm. The spraying device may be a gold-standard film sprayer. In the disclosure, the vancomycin-chicken egg albumin conjugate is sprayed to the front of the detection area on the nitrocellulose membrane, optionally including diluting the vancomycin-chicken egg albumin conjugate. The dilute solution may be a phosphate buffer. The concentration of the phosphate buffer may be 0.03-0.08 mol/L and preferably 0.05 mol/L. The pH of the phosphate buffer may be 7.0-7.5 and preferably 7.2.

In the disclosure, the vancomycin-chicken egg albumin conjugate may be prepared by the following method.

(1) the chicken egg albumin is mixed with the phosphate buffer to obtain a chicken egg albumin solution.

(2) the chicken egg albumin solution in step (1) vancomycin, 1-ethyl-3-(−3-dimethylaminopropyl)carbodiimide, and N-hydroxythiosuccinimide are mixed for a coupling reaction, and the coupled product is dialyzed against water to obtain a vancomycin-chicken egg albumin conjugate.

In the disclosure, the chicken egg albumin is mixed with the phosphate buffer to obtain a chicken egg albumin solution.

In the disclosure, the mass/volume ratio of the chicken egg albumin to the phosphate buffer is 8-12 mg:1-3 mL and preferably 10 mg:2 mL. The concentration of the phosphate buffer may be 0.05-0.15 M and preferably 0.1 M. The pH of the phosphate buffer may be 7.2-7.5 and preferably 7.4.

In the disclosure, after the chicken egg albumin solution is obtained, the chicken egg albumin solution, vancomycin, 1-ethyl-3-(−3-dimethylaminopropyl)carbodiimide, and N-hydroxythiosuccinimide are mixed for a coupling reaction, and the coupled product is dialyzed against water to obtain a vancomycin-chicken egg albumin conjugate.

In the disclosure, the ratio of the chicken egg albumin solution, vancomycin, 1-ethyl-3-(−3-dimethylaminopropyl) carbodiimide, and N-hydroxythiosuccinimide may be 1-3 mL:8-12 mg:2-4 mg:4-6 mg and preferably 2 mL:10 mg:3 mg:5 mg. The coupling time may be 0.5-1.5 h and preferably 1 h. The coupling temperature may be 18-26° C. and preferably 20° C. The coupling reaction may be carried out under stirring. The number of times of dialysis against water may be 3-7 and preferably 5. The storage temperature of the vancomycin-chicken egg albumin conjugate may be from −40° C. to −80° C. and preferably −70° C.

After the vancomycin-chicken egg albumin conjugate is obtained, the disclosure optionally further includes identifying the vancomycin-chicken egg albumin conjugate. The method for identifying includes the following steps: comparing the molecular weight of the vancomycin-chicken egg albumin with that of the chicken egg albumin. If the molecular weight of the vancomycin-chicken egg albumin conjugate is significantly greater than that of the chicken egg albumin, it is indicated that vancomycin has been successfully coupled to the chicken egg albumin. The method for determining the molecular weight may be Native SDS-PAGE electrophoresis.

In the disclosure, coating the quality control area with the goat anti mouse antibody may be carried out by the following method: spraying the goat anti mouse antibody onto the quality control area on the nitrocellulose membrane to form the quality control area. In the disclosure, the concentration of the goat anti mouse antibody may be 150-280 μg/mL and preferably 200 μg/mL. The spraying amount of the goat anti mouse antibody may be 1.0-1.5 μL/cm and preferably 1.2 μL/cm. The spraying device may be a gold-standard film sprayer. Before the goat anti mouse antibody is sprayed onto the quality control area on the nitrocellulose membrane, the disclosure optionally includes: the goat anti mouse antibody is diluted. The dilute solution may be a phosphate buffer. The concentration of the phosphate buffer may be 0.03-0.08 mol/L and preferably 0.05 mol/L. The pH of the phosphate buffer may be 7.0-7.5 and preferably 7.2.

The disclosure also provides an application of the test strips described in the scheme in the detection of vancomycin, including the following steps.

Pure vancomycin of different concentrations is added to a human serum matrix excluding vancomycin to prepare a calibrator. The concentrations of vancomycin in the calibrator is 40 μg/mL, 20 μg/mL, 10 μg/mL, 5 μg/mL, and 0 μg/mL, sequentially. The calibrator is diluted 100-1,000 times, and then loaded to a sample absorption pad of the test strip for immunochromatography, and a ratio (a T/C ratio) of the time-resolved fluorescent intensity of the detection area to the time-resolved fluorescent intensity of the quality control area is determined to obtain a function relation of the concentration of the calibrator and the T/C ratio.

A sample to be tested is taken and loaded to the sample absorption pad of the test strip for immunochromatography, a ratio of the time-resolved fluorescent intensity of the detection area to the time-resolved fluorescent intensity of the quality control area is determined, and the content of vancomycin in the sample to be tested is calculated according to the obtained function formula.

In the disclosure, if the fluorescence signal intensity is not detected in the quality control area, it is indicated that the operation process is incorrect or the test strip is expired.

In the disclosure, the sample to be tested may be added in an amount of 1-100 μL, preferably 20-90 μL, and more preferably 80 μL. The time of the immunochromatography may be 10-20 min and preferably 15 min. The temperature of the immunochromatography may be 20-25° C. and preferably 22-24° C. The device for determining the ratio of the time-resolved fluorescent intensity of the detection area to the time-resolved fluorescent intensity of the quality control area may be a fluorescence detector.

The following describes multiple exemplary embodiments of the time-resolved fluorescent immunochromatographic test strip for detecting vancomycin as well as the preparation method and application thereof.

Embodiment 1 A Preparation Method of a Time-Resolved Fluorescent Immunochromatographic Test Strip for Detecting Vancomycin 1. Synthesis and Identification of the Vancomycin Hapten-Carrier Protein Conjugate (1) Preparation of the Vancomycin-Bovine Serum Albumin Conjugate:

0.5 mL of ultrapure water in which 5 mg vancomycin is dissolved is added in 1 mL of 10 mg/mL NaIO4 solution, and the reaction is carried out by stirring at room temperature for 1 h in the dark. The reaction mixture is added to 1 ml of 5 mg/mL bovine serum albumin solution (50 mmol/L carbonate buffer with the pH of 9.6), adjusted to pH 9 with 1 mol/L Na2CO3 solution, stirred for 12 h, and dialyzed against water for 5 times, and stored at −70° C. for future use.

(2) Preparation of the Vancomycin-Chicken Egg Albumin Conjugate:

10 mg of chicken egg albumin is dissolved in 2 mL of 0.1 M phosphate buffer with the pH of 7.4, 10 mg of vancomycin is added to the foregoing solution to be uniformly stirred, and then 3 mg of 1-ethyl-3-(−3-dimethylaminopropyl)carbodiimide and 5 mg of N-hydroxythiosuccinimide are added and dissolved in the foregoing solution, and stirred at room temperature and reacted for 1 h. Dialysis against water is carried out for 5 times, and storage is carried out at −70° C.

(3) Identification of Vancomycin Hapten-Carrier Protein Conjugate

Molecular weight analysis of four proteins, i.e., the bovine serum albumin, the vancomycin-bovine serum albumin conjugate, the chicken egg albumin, and the vancomycin-chicken egg albumin conjugate, is simultaneously performed by Native SDS-PAGE electrophoresis. The results show that the molecular weight of the vancomycin-bovine serum albumin ovalbumin peptide is significantly greater than that of the bovine serum albumin, and the molecular weight of the vancomycin-chicken egg albumin ovalbumin peptide is significantly higher than that of the chicken egg albumin, indicating that vancomycin has been successfully coupled to the bovine serum albumin and the chicken egg albumin.

2. Preparation of the Vancomycin Monoclonal Antibody

The prepared vancomycin-bovine serum albumin immunogen is immunized with Balb/c by a conventional method, and the Balb/c mouse spleen cells which produce specific antibodies are fused with myeloma cells SP20 after intensive immunization, and an indirect competitive enzyme-linked immunoassay method is used to determine the cell supernatant, and positive wells are screened. The positive wells are cloned by using a limiting dilution method to obtain and establish a monoclonal antibody-producing hybridoma cell line.

Balb/c mice (8 weeks old) are intraperitoneally injected with sterile paraffin oil, and hybridoma cells are intraperitoneally injected 7-14 days later, and ascites is collected 7-10 days later. The ascites is purified by the octanoic acid-saturated ammonium sulfate method, the purity is identified by SDS-PAGE electrophoresis, and storage is carried out at −20° C.

3. Preparation of the Fluorescent Microsphere Labeled Vancomycin Monoclonal Antibody (1) Activation: 100 uL of microsphere suspension internally embedded with a fluorescent dye and modified with a carboxyl functional group at the surface purchased from Nanjing Microdetection Bio-Tech Co., Ltd. is suspended in 400 uL of activation buffer (50 mM MES with the pH of 6.0), and 0.5 mg of EDC and 0.5 mg of NHS are added, and the mixture is shaken and activated at room temperature for 15 min after mixing.

(2) Coupling: the suspension of (1) is centrifuged at 4° C., 10,000 r/min for 10 min, the supernatant is discarded, re-suspension is carried out in the activation buffer, 2 ug of vancomycin monoclonal antibody solution is added, and the mixture is shaken and coupled at room temperature for 120 min after mixing.

(3) Blocking: the suspension of (2) is added to 100 ul of 10% bovine serum albumin solution, and the mixture is shaken and blocked overnight at room temperature after mixing.

(4) Storage: the suspension of (3) is centrifuged at 4° C., 10,000 r/min for 10 min, the supernatant is discarded, and re-suspension is carried out in a storage buffer (a PB buffer containing 0.01% NaN3 and 0.1% bovine serum albumin with the pH of 7.4), the microspheres are washed once, and the mixture is stored at 4° C. in the dark after mixing.

4. Preparation of the Fluorescent Microsphere Pad

The stored fluorescent microsphere-labeled vancomycin monoclonal antibody is diluted to 2 μg/mL in the storage buffer, and then sprayed with a gold-standard film sprayer, dried at 37° C. for 15 h, and taken out and sealed for storage.

5. Preparation of a Nitrocellulose (NC) Membrane Coated with Antibodies

The vancomycin hapten-chicken egg albumin conjugate is diluted to 200 ug/mL with 0.05 mol/L of PB buffer with the pH of 7.2, and sprayed on the detection area (T) of the NC membrane with the gold-standard film sprayer with the quantity for spray of 1.2 uL/cm. The goat anti mouse antibody is diluted to 200 ug/mL with 0.05 mol/L of PB buffer with the pH of 7.2, and sprayed onto the detection area (C) of the NC membrane with the gold-standard film sprayer with the quality for spray of 1.2 uL/cm, and dried at 37° C. for 5 h for future use.

6. Preparation of a Sample Absorption Pad

The sample absorption pad is soaked in 0.1 mol/L of phosphate buffer with the pH of 7.2 containing 0.5% bovine serum albumin (volume fraction) for 2 h, and dried at 37° C. for 2 h for future use.

7. Assembly of a Test Strip

The sample absorption pad, the glass fiber pad, the NC membrane, and the absorbent pad are sequentially overlapped and immobilized from left to right on the bottom plate, the end of the sample absorption pad is connected to the beginning of the glass fiber pad, the end of the glass fiber pad is connected to the beginning of the NC membrane, the end of the NC membrane is connected to the beginning of the absorbent pad, the beginning of the sample absorption pad is aligned with the beginning of the bottom plate, and the end of the absorbent pad is aligned with the end of the bottom plate, and then cut into a small strip with a width of 3.96 mm by a machine to be packed in special plastic cards to form a test strip.

Embodiment 2 Application of the Test Strip of Embodiment 1

1. Sample Pretreatment 20 ul of sample is accurately pipetted into 180 ul of sample diluent and mixed fully.

2. Detection with the Test Strip 80 uL of sample solution to be tested is accurately pipetted into a test strip loading well with a micropipette, and reaction is carried out at 20° C. for 15 min. The test strip is inserted into a load carrier of a fluorescence detector, an item to be tested is selected by touching a display screen, a "Detection Start" button is pressed, the fluorescence detector automatically scans the test strip, and a test result is read through the display screen of an instrument or printed.

3. Analysis of Test Results

Quantitative Detection

After the test is completed, the instrument obtains the ratio of the time-resolved fluorescent intensity of the detection area on the test strip to the time-resolved fluorescent intensity of the quality control area, and calculates the content of vancomycin in the sample to be tested according to the following formula.

$$Y=(A-D)/[1+(x/C)^{\wedge}B]+D$$

In the formula, A=0.44001, B=0.57869, C=3.22910, and D=0.16687. Y is the ratio of the time-resolved fluorescent intensity of the detection area on the test strip to the time-resolved fluorescent intensity of the quality control area, and X is the concentration of vancomycin in the sample.

Expiration: if the fluorescence signal intensity is not detected in the quality control area, it is indicated that the operation process is incorrect or the test strip is expired.

Embodiment 3 Measurement of Cross-Reaction Rate of the Test Strip of Embodiment 1

Several vancomycin analogs and common drugs are selected for interference testing. The following various compounds are added to a human serum sample with the vancomycin concentration of 20 μg/mL, and the sample is tested using the test strip of Embodiment 1, and the test results of the sample added with the compound are compared with the results of the control sample. See Table 1 for the test results. The results show that the vancomycin test strip of Embodiment 1 of the disclosure has high specificity and does not cross-react with various drugs.

TABLE 1

Results of cross-reaction rate measurement of the test strip of Embodiment 1

| Compound name | Test concentration | Cross reaction rate |
| --- | --- | --- |
| Vancomycin | 20 μg/mL | 100% |
| Norvancomycin | 100 μg/mL | <1% |
| Salicylic acid | 1,000 μg/mL | <0.001% |

TABLE 1-continued

Results of cross-reaction rate measurement of the test strip of Embodiment 1

| Compound name | Test concentration | Cross reaction rate |
|---|---|---|
| Aspirin | 1,000 µg/mL | <0.001% |
| Valproic acid | 1,000 µg/mL | <0.001% |
| Carbamazepine | 1,000 µg/mL | <0.001% |
| Digoxin | 1,000 µg/mL | <0.001% |
| Phenytoin | 1,000 µg/mL | <0.001% |
| Theophylline | 1,000 µg/mL | <0.001% |

$$\text{Cross reaction rate} = 100 \times \frac{\text{Test results of the sample added with compounds} - \text{Results of the control sample}}{\text{Concentration of the added cross reactant}}$$

Embodiment 4 Correlation Analysis of Test Results of the Test Strip of Embodiment 1 of the Disclosure The test strip of Embodiment 1 of the disclosure is compared with the method for determining vancomycin in human serum by high performance liquid chromatography. The human serum is a clinical serum sample. The high performance liquid chromatography is carried out as follows: Waters 2695 High Performance Liquid Chromatograph, C18 column (150 mm×4.6 mm, 5 µm), mobile phase: 50 mmol/L potassium dihydrogen phosphate buffer-acetonitrile with the pH of 3.2 (90:10), detection wavelength: 230 nm, flow rate: 1 mL/min, and 400 µl of serum sample is added with 50 µl of 10% zinc sulfate precipitated protein, and after centrifugation at 5000 r/min, 20 µl of the sample is taken to determine the peak height of vancomycin. The results are shown in Table 2. The correlation curve is shown in the FIGURE, which shows that the two fit well.

TABLE 2

Comparison of the method for determining the vancomycin in human serum by the test strip of Embodiment 1 of the disclosure and the high performance liquid chromatography

| Serum sample No. | Fluorescent immunochromatography (µg/mL) | High performance liquid chromatography (µg/mL) |
|---|---|---|
| Sample 1 | 0.4 | 0.5 |
| Sample 2 | 1.1 | 1.2 |
| Sample 3 | 1.6 | 1.9 |
| Sample 4 | 2.4 | 2.1 |
| Sample 5 | 3.5 | 4.2 |
| Sample 6 | 5.2 | 5.9 |
| Sample 7 | 6.4 | 7.1 |
| Sample 8 | 8.5 | 8.6 |
| Sample 9 | 9.2 | 9.8 |
| Sample 10 | 11.1 | 10.2 |
| Sample 11 | 14.2 | 15.2 |
| Sample 12 | 15.2 | 17.2 |
| Sample 13 | 16 | 15.4 |
| Sample 14 | 17 | 18 |
| Sample 15 | 19.1 | 19.9 |
| Sample 16 | 19.8 | 20 |
| Sample 17 | 21 | 22 |
| Sample 18 | 23 | 24 |
| Sample 19 | 32 | 34 |
| Sample 20 | 25 | 24 |
| Sample 21 | 28 | 30 |
| Sample 22 | 30 | 32 |
| Sample 23 | 35 | 38 |
| Sample 24 | 46 | 40 |
| Sample 25 | 56.1 | 52 |

Various embodiments of the disclosure may have one or more of the following effects. The time-resolved fluorescent immunochromatographic test strip may be used for detecting vancomycin. The test strip may have no cross reaction with various vancomycin analogs. The test strip may have the advantages of high detection accuracy and strong specificity. The test strips may use a vancomycin-bovine serum albumin conjugate as an immunogen, and may have strong specificity and good immunogenicity. The prepared vancomycin monoclonal antibody may have strong specificity and high titer. The test strip may improve the stability of fluorescence detection, eliminate the interference of the fluorescent substance in the environment to an object to be tested, reduce the background fluorescent intensity, and/or improve the resolution. Some experiment results show that the test strip may have no cross reaction with various vancomycin analogs, and may have high detection accuracy and strong specificity.

The foregoing descriptions are only exemplary implementation manners of the present invention. It should be noted that for a person of ordinary skill in the art, several improvements and modifications may further be made without departing from the principle of the present invention. These improvements and modifications should also be deemed as falling within the protection scope of the present invention.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various FIGURES need be carried out in the specific order described.

The disclosure claimed is:

1. A test strip-based detection method of vancomycin, comprising the steps of:
   (1) adding pure vancomycin of different concentrations to a human serum matrix excluding vancomycin to prepare a calibrator, concentrations of vancomycin in the calibrator being 40 µg/mL, 20 µg/mL, 10 µg/mL, 5 µg/mL, and 0 µg/mL, sequentially;

(2) diluting the calibrator 100-1,000 times and loading the diluted calibrator to a sample absorption pad of a test strip for immunochromatography;
(3) determining a T/C ratio of a time-resolved fluorescent intensity of a detection area to the time-resolved fluorescent intensity of a quality control area to obtain a function relation of the concentration of the calibrator and the T/C ratio;
(4) taking a sample to be tested and loading the sample to the sample absorption pad of the test strip for immunochromatography;
(5) determining a ratio of the time-resolved fluorescent intensity of the detection area to the time-resolved fluorescent intensity of the quality control area; and
(6) calculating a content of vancomycin in the sample to be tested according to the function relation.

2. The method according to claim 1 wherein the sample to be tested is loaded in an amount of 1-100 µL.

\* \* \* \* \*